US005437268A

United States Patent [19]

Preece

[11] Patent Number: 5,437,268

[45] Date of Patent: Aug. 1, 1995

[54] DIVING REGULATOR DEMAND VALVE WITH BAFFLES TO REDUCE BREATHING EFFORT AND VENTURI ADJUSTING MEANS

[75] Inventor: Kim Preece, Manly Vale, Australia

[73] Assignee: T.D. Preece & Co. Pty. Ltd., Manly Vale, Australia

[21] Appl. No.: 71,946

[22] Filed: Jun. 3, 1993

Related U.S. Application Data

[63] Continuation of Ser. No. 654,659, filed as PCT/AU90/00249, Jun. 6, 1990, abandoned.

[30] Foreign Application Priority Data

Jun. 6, 1989 [AU] Australia .............................. PJ4577

[51] Int. Cl.$^6$ ........................ A61M 16/00; A62B 7/04; F16K 31/26; F16K 17/20

[52] U.S. Cl. .......................... 128/205.24; 128/201.28; 128/204.26; 137/469; 137/494

[58] Field of Search ...................... 128/201.28, 204.26, 128/205.24, 204.25; 137/469, 494, 495

[56] References Cited

U.S. PATENT DOCUMENTS

| | | | |
|---|---|---|---|
| 2,571,007 | 10/1951 | Biggert, Jr. | 137/469 |
| 2,667,893 | 2/1954 | Kupiec | 137/494 |
| 2,767,726 | 10/1956 | Feucht | 137/494 |
| 3,028,860 | 4/1962 | Gagnan et al. | 128/202.22 |
| 3,044,484 | 7/1962 | Dunning | 137/469 |
| 3,053,271 | 9/1962 | Crittenden, Jr. et al. | 137/494 |
| 4,076,041 | 2/1978 | Christianson | 128/204.26 |
| 4,616,645 | 10/1986 | Pedersen et al. | 128/204.25 |
| 4,796,618 | 1/1989 | Garraffa | 128/204.25 |
| 4,798,202 | 1/1989 | Chambonnet | 128/204.25 |
| 4,834,086 | 5/1989 | Garofalo | 128/204.18 |
| 4,889,115 | 12/1989 | Bozano | 128/204.26 |

*Primary Examiner*—Kimberly L. Asher
*Attorney, Agent, or Firm*—Townsend and Townsend Khourie and Crew

[57] ABSTRACT

A breathing regulator for use in underwater breathing comprising a diaphragm and poppet actuated upon user demand. The poppet including at least one baffle located intermediate its ends wherein when air is demanded by a user of the regulator air travels through the valve and continuously impinges upon the baffle and reduces the effort of the user required to operate the valve. The regulator further comprises a sleeve which is concentric about the air passage chamber which facilitates more efficient air delivery to the user. The sleeve is selectively controlled by the user either to enhance the venturi flow of air or to cancel the venturi effect, dependent upon the needs of the user.

20 Claims, 3 Drawing Sheets

DIVING REGULATOR DEMAND VALVE WITH BAFFLES TO REDUCE BREATHING EFFORT AND VENTURI ADJUSTING MEANS

This is a continuation of application Ser. No. 07/654,659, filed as PCT/AU90/00249, Jun. 6, 1990, now abandoned.

The present invention relates to self contained underwater breathing apparatus and more specifically relates to improvements in regulators associated therewith whereby the breathing characteristics in a regulator are altered so as to reduce the inhalation effort required by a user upon demand for air. The alteration in the breathing characteristics is effected according to the present invention by adjustments to the demand valve in the regulator.

Regulators are well known in the diving industry as a crucial component of the apparatuses required. A regulator acts in concert with a pressure reducing valve and as a means for regulation of air for a diver. The pressure reduction activity is known as the first stage of regulation and this involves the reduction in air pressure between the air tank and the regulator. The supply of air upon demand by a diver passes through the first stage thence through a second stage.

It is the second stage of operation to which the present invention is primarily directed.

The second stage of operation is controlled by a demand valve which is located near the air discharge end of the regulator which comprises a mouthpiece.

It is one object of the present invention to reduce the effort required on the part of the user of the regulator upon demand for air.

Regulator are well known with numerous designs for those being readily available. In its most basis form a typical regulator comprises a housing having a mouthpiece and a demand valve which acts in concert with a vacuum assisted diaphragm located inside the housing. The diaphragm is, and consequently the demand valve, are operably responsive to demand for air. The demand valve is typically adapted with an internal element known as a poppet which is adapted to operate between a closed and open position in response to demand for air by a user.

The poppet when in the closed position, is urged against an air inlet hole in the valve under the assistance of a spring bias closing off the supply of air via the inlet. The compression force in the spring must be at least slightly greater than the pressure exerted immediately upstream of the inlet orifice to enable the closing of the orifice.

The poppet moves from the closed configuration to an open configuration upon demand for air. When the poppet is open unbalanced forces are generated due to the gradient of increasing effort required to overcome the increasing compressive force exerted by the spring bias when demand is made for air by the user.

When a user of a regulator demands air the initial inhalation effort is called the cracking effort. That is, the effort required to move the sealing end of the poppet away from the air inlet. The cracking effort required is generally a function of the dynamic air pressure acting on the end of the poppet at the air inlet end of the valve relative to the energy in the biasing spring coupled with the degree of vacuum required to overcome the counteracting spring force upon demand for air.

The air travel is also affected by a venturi effect created when air is demanded due to the high velocity of the air.

The prior art poppet arrangement suffers from the major disadvantage that an unbalanced force regime is generated at the air entry orifice and within the valve chamber due to the prior art configuration of the typical poppet.

In the prior art arrangement, when the diver breathes the forces become unbalanced due to the fact that the poppet is in the open position and also due to the fact that the line pressure of the air does not bear sufficiently on the poppet to reduce breathing effort. In this case, full reliance must be placed on the vacuum to maintain the poppet in the open position. This requires considerable effort with this increasing to its maximum at a time when the inhalation of the user is at its weakest that is at the end of the breathe in cycle.

The present invention seeks to ameliorate or eliminate the unbalanced forces existing in the prior art demand valves by providing a newly configured demand valve which results in balanced forces in the valve and a reduced effort on the part of the user when demanding air.

In a further improvement to demand valve, the valve is adapted with a concentric sleeve operable by a knob external of the housing to enable adjustment by a user when in use of the air passage such that the vacuum can be cancelled to conserve air or to adjust venturi flow so as to direct air into the mouthpiece of the regulator. The prior art regulators could only be adjusted by use of a screw driver or like instrument.

In one broad form the present invention comprises a demand valve of the type comprising an air passage chamber, an inlet port and an outlet port and having disposed therein a poppet biased against the inlet port, characterised in that the poppet comprises a first flange and second flange for receiving line pressure and/or deflection of air passage, wherein when said demand valve is in use and vacuum assisted air from said inlet port impinges upon and is urged against said first means, air also from said inlet impinges on said second flange and is contemporaneously deflected by said second flange so that air leaves the said valve said outlet port thereby reducing the effort required by the user upon demand for air to overcome the biasing force.

In its broadest form the present invention comprises;

A breathing regulator for use in underwater breathing of the type comprising;

a primary housing with a breathing chamber and adapted with a valve enabling travel of air upon demand by a user from an inlet to an outlet in the valve thence to an outlet in the housing via a mouth piece to the lungs of user, a movable diaphragm for creating a vacuum in the housing responsive to demand for air, characterised in that the valve comprises a poppet slidably mounted therein and acting against a bias and comprising an elongated member having first and second ends; and, at least one air baffle on or integral with said elongated member, located intermediate said ends wherein when air is demanded by a user of the regulator air travels through said valve and continuously impinges upon said at least one baffle thereby reducing the effort of the user required to operate the valve upon demand for air.

In the preferred embodiment the demand valve also comprises a sleeve which is concentric about the air passage chamber. The purpose of the drum is to facilitate more efficient air delivery to the user following exiting of the air from the housing. The drum also enables selective control of air by the user external of the housing to either enhance the venturi flow of air or to cancel the effect of the vacuum according to user requirements.

The invention will now be described in more detail according to a preferred but non limiting embodiment and with reference to the accompanying illustrations wherein;

FIG. 1 shows an abbreviated longitudinal sectional view of a prior art demand valve with the valve poppet shown in the closed configuration, FIG. 2 shows an abbreviated longitudinal sectional view of a prior art demand valve with the valve poppet shown in the open configuration, FIG. 3 shows an abbreviated longitudinal sectional view of a demand valve according to one embodiment of the present invention with the valve poppet shown in the closed position, FIG. 4 shows an abbreviated longitudinal sectional view of a demand valve according to one embodiment of the present invention with the valve poppet shown in the open position, FIG. 5 shows a cross sectional plan view of a regulator with demand valve and with the poppet in the closed configuration.

Figure 1:
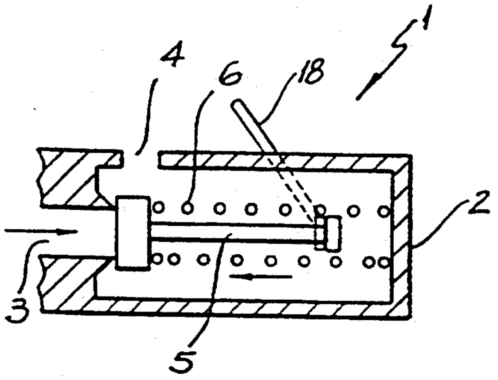
FIG. 1 PRIOR ART

Referring to FIG. 1 there is shown a portion of a prior art demand valve 1 comprising a housing 2 having an inlet opening 3 and an outlet opening 4. The demand valve also comprises within the housing a poppet 5 shown in the closed position and being urged against the mouth of orifice 3 under the biasing action of helical spring 6.

Figure 2:
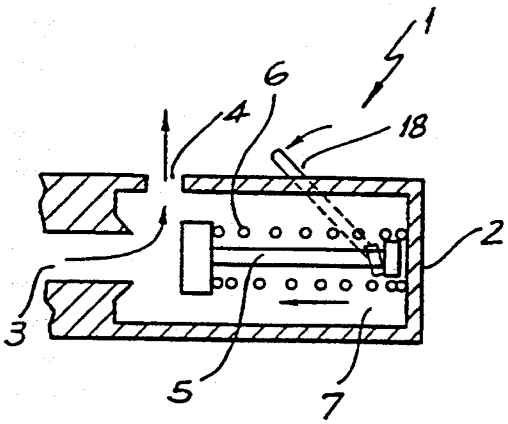
FIG. 2 PRIOR ART

FIG. 2 shows the demand valve of FIG. 1 however, this time the poppet 5 is shown drawn away from the area of inlet opening 3 so as to enable air to pass within cavity 7 of the housing 2. In the configuration of the demand valve found in FIG. 1, the force regime is such that the compressive force generated by the spring 6 is at least slightly larger than the force generated by the air pressure at the inlet opening 3. This results in the poppet 5 being urged against the opening 3 to thereby close off the opening when air is not required.

When a user of a prior art regulator having the demand valve with poppet 5 contained therewithin draws breath in order to obtain air, a vacuum is created which causes a diaphragm to engage with lever 18 to enable air to pass into the chamber 7. At the same time the poppet 5 is drawn back against the spring bias allowing the air to pass through the chamber 7 and exit via opening 4. AT this moment the demand valve force regime becomes unbalanced because the spring bias force gradually increases due to increasing compression of the spring. This has a resultant effect of decreasing the opposing air inlet line force on poppet 5 generated by the ingress of air through opening 3. This consequently results in a decrease in the air pressure on the poppet. This is also exacerbated by the effect that air is at the same time escaping through outlet opening 4. As a result of this force regime, the effort in order to maintain air flow during the activity of drawing breath to demand air gradually increases over a gradient thereby requiring greater force to be exerted to maintain the poppet 5 in the open position. This occurs at the time when the energy of the user during inhalation is at its weakest; that is at the end of the inhalation.

It is therefore desirable to provide a demand valve having improved facility for creating a reduction in effort necessary to be exerted by a user upon demand for air.

Figure 3:
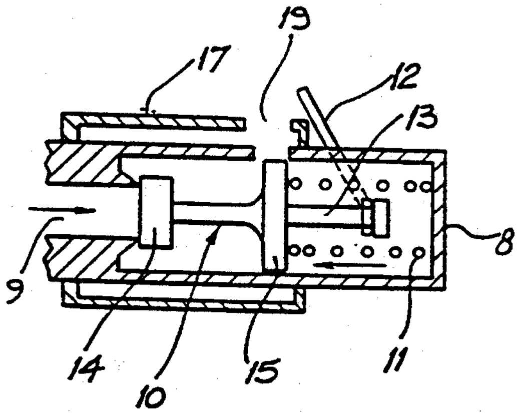

FIG. 3 shows a portion of a demand valve according to the preferred embodiment of the present invention showing a newly configured poppet valve 10 and an externally adjustable outer concentric sleeve 17 which assists in directing air flow to the mouth of the user.

The demand valve of FIG. 3 comprises a valve housing 8 having there within an inlet orifice 9 similar to the inlet orifice 3 of the prior art valve in FIG. 1. The valve also contains a poppet 10 which is urged against the orifice of inlet opening 9 under the assistance of biasing spring 11. The valve also has a conventional lever 12 which is actuated by linkage to the valve and which is responsive to the action by vacuum assistance of a regulator diaphragm (see FIGS. 5 and 6) upon demand for air by a user of the demand valve.

Figure 4:
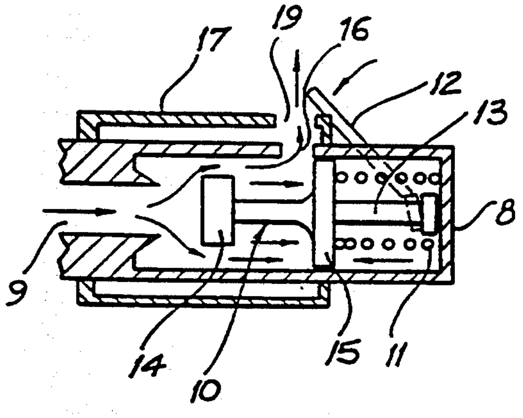

The demand valve of the present invention differs in one respect from the prior art according to one embodiment by firstly comprising a newly configured poppet 10. As can be seen from FIG. 3 the poppet 10 comprises an elongated shaft 13 having located thereon or thereabout a first baffle or flange 14 and a second baffle or flange 15. The configuration of this poppet results in a change in the force regime which occurs around the poppet upon demand for air by a user of the demand valve. FIG. 3 shows the demand valve according to the present invention with the poppet in the closed position. When a user demands air, the action of the diaphragm in the regulator (not shown) causes arm 12 to allow passage of air through inlet opening 9. The configuration of the demand valve in the open position is shown in FIG. 4. When air is demanded by a user, the air travels through passage 9 as previously stated. The passage of this air which is under pressure causes a number of effects. The first being counteraction of the force exerted by biasing spring 11, the second being the impingement of air upon the broad face of flange or baffle 14 and a deflection of air around flange or baffle 15.

The effect of the forces so generated cause an increase of an/or a maintenance of pressure in the flange or baffle 15 at the same time as deflection of air is caused by and about flange 14. At this time air is also escaping via outlet orifice 16 located in the wall of the housing 8 and via orifice 19 located in concentric sleeve 17. The configuration of the poppet 10 is such that the air can only either escape through exit 16 or alternatively impinge upon the surface of baffle 15. The impingement of the air on baffle 15 has the effect of countering the increase in the size of the biasing force exerted by spring 11 as it is compressed under the action of the air pressure. The impinging air on baffle 15 also compensates for air loss through orifice 16. The overall result of this effect is to reduce the effort required by the user demanding air due to the air line forces being maintained on the poppet thereby enabling optimum force balance.

Figure 5:
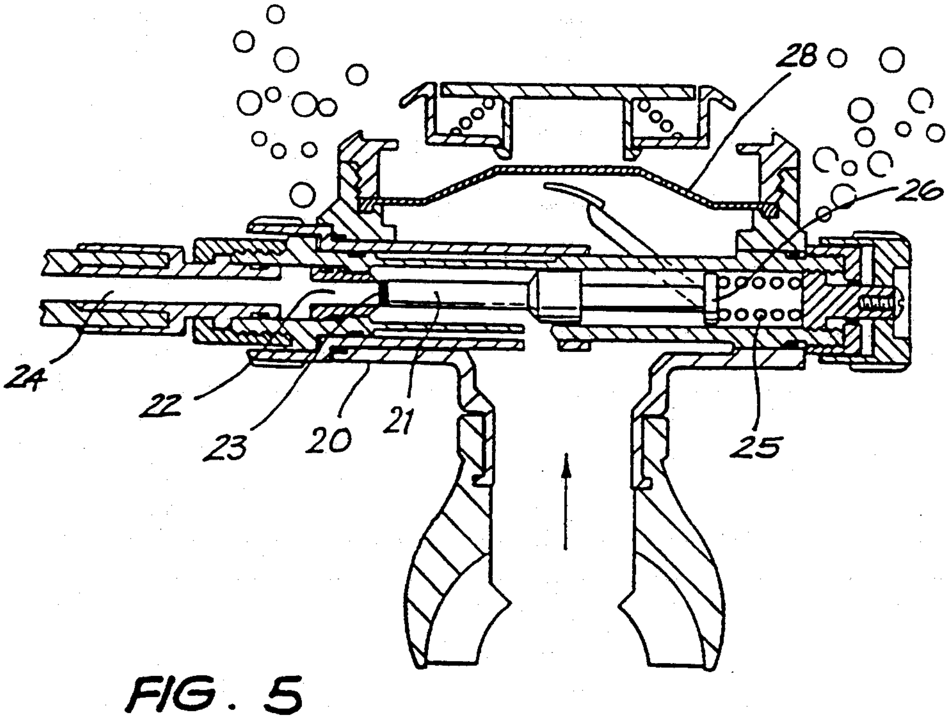

Referring to FIG. 5 there is shown a cross sectional plan view of a regulator having a demand valve 20 shown in the configuration commensurate with exhalation by a user. In this configuration the demand valve 20 is shown poppet 21 urged against orifice 22 such that the orifice 22 is sealed by poppet end 23. Line pressure from a supply tank (now shown) is exerted in supply line 24 usually the line pressure exerted in line 24 would be at or around 28 pounds force. In order to counteract this force, biasing spring 25 urges the end of the poppet 26 in a direction contrary to that exerted by the line pressure on the end 23 of the poppet 21.

Ideally the pressure exerted by the biasing spring 25 should be as close as possible to the line pressure but slightly above the line pressure so that when air is not demanded the poppet remains in the closed configuration.

Figure 6:
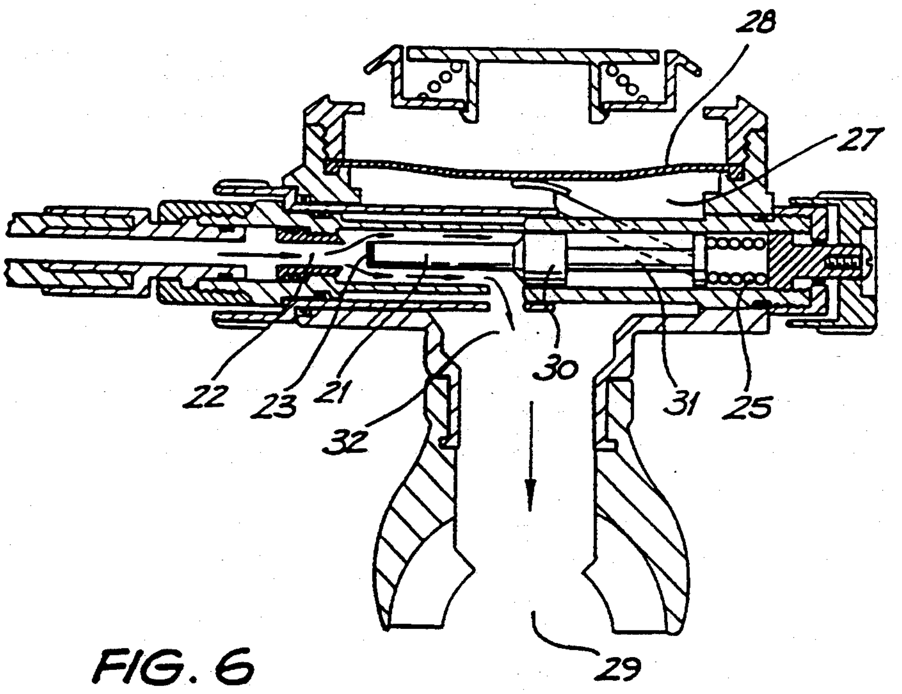
FIG. 6 shows a cross sectional plan view of a regulator with demand valve and with the poppet in the open configuration.

FIG. 6 shows the regulator of FIG. 5 this time in the air demand or inhalation configuration when a user demands air. Upon demand for air the end 23 of the poppet 21 is drawn away from the orifice under the assistance of the vacuum created in chamber 27 by diaphragm 28.

As the spring bias force is ideally slightly greater than the line pressure, a further effort is required to be exerted on the poppet 21 to move it away from the orifice 22 to thereby allow free flow of air to mouthpiece 29. In order to assist this process, the flange 30 which is located around the main shaft 31 of the poppet 21.

In the prior art poppet arrangement the line pressure had no effect in urging a force against the poppet once the poppet had released from the supply orifice. According to the preferred embodiment of the present invention, the provision of the flange 31 provides a surface on which the incoming air can impinge thereby enabling retention of the line pressure on the poppet to urge the poppet away from the inlet orifice thereby reducing the effort required by the user upon demand for air.

Although FIGS. 5 and 6 show a flange on the poppet according to one embodiment it is envisaged that the flange can be made upon from one or more of a plurality of flanges provided obstruction is provided to the air incoming from the orifice 22 and passage via orifice 32 to the mouthpiece 29. Ideally the flange would be located when the poppet is in the fully open configuration at or near orifice 32 so that air is contemporaneously impinging on the flange 31 and redirected via orifice 32 into the mouthpiece 29.

This results in the system having a balanced force regime in the valve and between the biasing force and the line pressure impinging on the baffles thereby reducing the effort required by the user upon the demand for air. One advantage of the existence of the flange or baffle means on the poppet is that spring selection is not as critical as it has been in prior art valves when unbalanced forces are introduced into the breathing system upon demand for air.

Thus, the line pressure which is exerted on the end 23 of the poppet 21 when in the closed position is maintained on the poppet but transferred when the poppet is in the open position to impinge on flange 30. In addition to the altered configuration of the poppet valve, the improved valve also comprises a concentric sleeve 17 (see FIGS. 3 and 4) adapted to concentrically rotate about housing 8. Alternatively, the housing 8 may be fixedly attached to the sleeve 17 so that the whole demand valve portion can rotate as one. This allows the facility for directing the air towards the mouth piece of the regulator thus facilitating improved passage of air and without the assistance of baffles as was required in the prior art.

Figure 7:
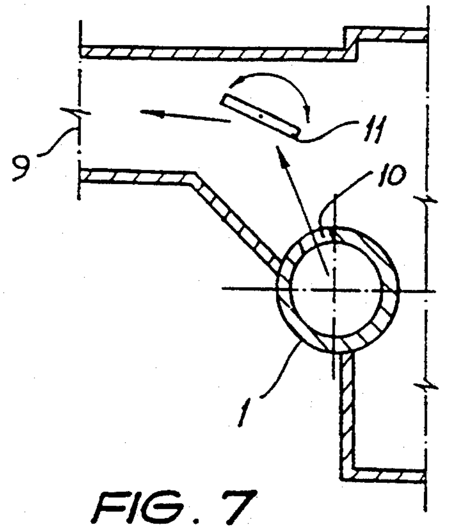
FIG. 7 PRIOR ART
FIG. 7 shows an abbreviated cross sectional view of a prior art regulator showing the baffle used for deflection of air.

FIG. 7 shows an abbreviated cross sectional elevational view of the prior art configuration of the regulator showing a baffle used for deflection of air. The attitude of the baffle is selected according to the angle the air is to impinge on the baffle.

Figure 8:
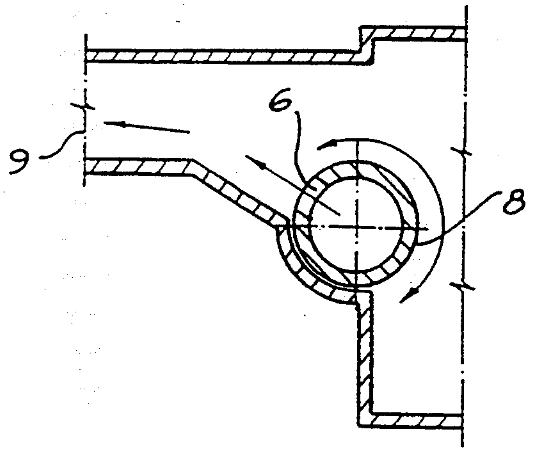
FIG. 8 shows an abbreviated cross sectional view of a regulator according to one embodiment of the invention showing the concentric sleeve.

FIG. 8 shows a cross sectional view of a regulator showing the venturi assist facility in the demand valve of the present invention located therein. Also in this regulator, it can be noted that the baffle is absent with the air being directed via rotational freedom of the demand valve so that the user may select the direction of air which leaves the demand valve, according to air demand requirements.

The disadvantage of the baffle arrangement for air delivery as shown in FIG. 7 in the cross section of the regulator is that the baffle or screen can work to obstaculate the passage of air towards the mouth piece of the regulator. It can also result in drag on the air due to the change in direction thus slowing down entry of the air into the mouth piece of the regulator. This problem is overcome by the elimination of the baffle and also by the facility imparted to the demand valve of the present invention whereby it can be rotated within the regulator by external selective orientation of the directional passage of air towards the mouth piece of the regulator. With the rotational ability of the demand valve as shown in FIG. 6, it is possible that air could be directed any where within the range of 0° to 360° thereby resulting in freer passage of air to the mouth of a user.

Figure 9:
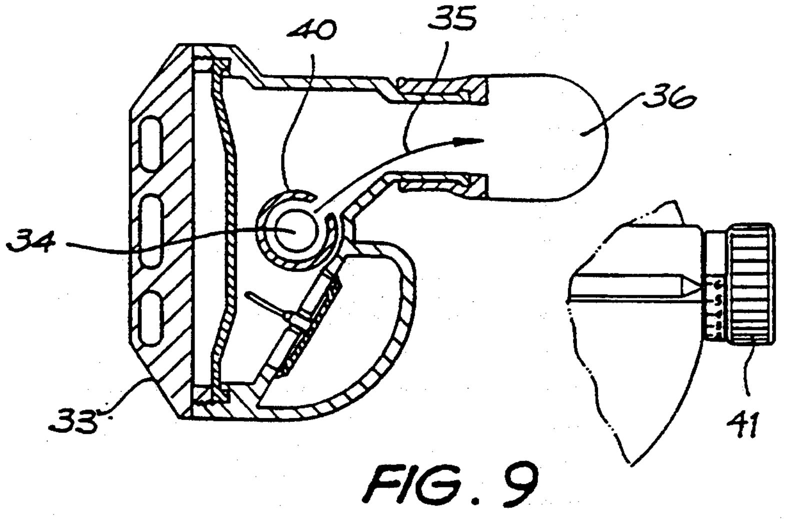
FIG. 9 shows a side elevational view of a regulator with the externally operable concentric sleeve of the maximum flow configuration.

Referring to FIG. 9 there is shown a side elevational cross sectional view of a regulator 33 having a demand valve 34 whereby air exists the demand valve in the direction of arrow 35 into the mouthpiece 36.

Figure 10:
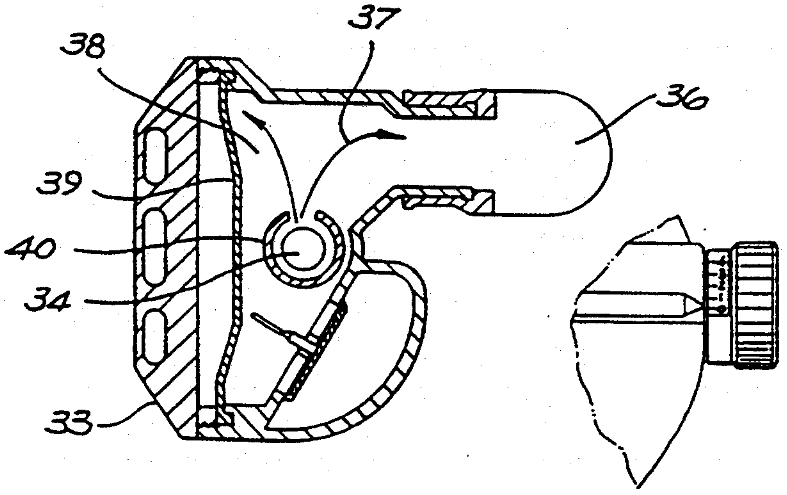
FIG. 10 shows a side elevational view of the regulator of FIG. 9 with the externally operable concentric sleeve in the minimum flow configuration.

FIG. 10 shows the regulator 33 this time with the demand valve 34 reconfigured so that air travels in the direction of arrows 37 so that the vacuum effect created in chamber 38 by means of diaphragm 39 is counteracted. A control of the demand valve 34 is effected by means of a sleeve 40 which is operable by means of a knob 41 which is external to the regulator 33. This enables a user to alter the direction of air in the mouthpiece during use.

According to the prior art methodology, such adjustment could only be effected by using an instrument to gain access to the inside of the regulator to select a air direction configuration prior to use.

The demand valve arrangement of the present invention enables a user to make an air boost selection at any time during use by means of the external knob 41. This enhances a venturi effect of high velocity air when required and it may also counteract the vacuum effect created in chamber 38 by diaphragm 39 when a user demands air through the mouthpiece 36.

Thus, FIG. 9 shows the configuration of the demand valve 34 when maximum air delivery would be presented to mouthpiece 36.

FIG. 9 shows the demand valve 34 with the configuration of sleeve 40, disposed so that air delivery to mouthpiece 36 is at a minimum. A selection of the configuration as shown in FIG. 10 would be likely to be made by an operator when less air is required.

Different users have different air requirements to maintain a comfortable breathing rate when diving. Thus, it is desirable to have a manual air delivery control which can be adjusted during use according to the particular circumstances.

As a diver dives deeper, the density of air increases necessitating ideally a facility for compensating adjustment to the air delivery. The improvement to the demand valve 34 enables this to be achieved. Also, the adjustment enables unwanted free flow of air to be prevented or minimised where necessary.

Furthermore, it has been found by divers that too much air can lead to nausea and discomfort when diving. The improvement to the demand valve can stop this by restricting the amount of air free flowing to the user thus, the valve can be adjusted to personal requirements according to air demand.

It will be recognised by persons skilled in the air that numerous variations and modifications may be made to the present invention without departing from the overall spirit and scope of the invention as broadly described herein.

I claim:

1. In a breathing regulator for use in underwater breathing through the mouth of a user including;

a primary housing with a breathing chamber having an inlet and an outlet;

a valve across the primary housing blocking the inlet and the outlet when closed and enabling travel of air between the inlet and the outlet upon demand by the user and thence from the housing via a mouthpiece to the mouth of the user;

a movable diaphragm in the primary housing responsive to demand for air from the user;

the improvement to the valve across the housing comprising:

a flow path within the primary housing between the inlet and the outlet;

a poppet slidably mounted in the flow path to open and close the flow path, the poppet including an elongated member having first and second ends with a first air baffle at one of the ends;

means for providing a bias on the poppet to normally close the flow path, the poppet when urged against the bias opening the flow path; p1 means connecting the moveable diaphragm and the poppet for moving the poppet responsive to the moveable diaphragm;

at least one second air baffle on the elongated member, located intermediate the first and second ends in the flow path, air, responsive to demand of the user traveling through the valve and continuously impinging upon the at least one second baffle and reduces the effort of the user required to operate the valve upon demand for air; and, means for venturi assisted air direction through the valve comprising a hole in the primary housing of the valve and rotatable concentric sleeve about the primary housing and with an opening therein which selectively aligns with the hole to direct and throttle the free flow of air through the valve.

2. A regulator according to claim 1 wherein the first end of the elongate member of the poppet operates to alternatively prevent and allow passage of air from an inlet line to a chamber in the valve responsive to demand for air.

3. A regulator according to claim 2 including means for connecting the diaphragm and poppet with a lever arm engaging the second end of the elongate member of the poppet which operates the poppet in response to movement of the diaphragm.

4. A regulator according to claim 1 wherein the rotatable concentric sleeve is operable via a knob external of the valve.

5. A regulator according to claim 1 wherein:

the rotatable concentric sleeve is operable via a knob external of the valve; and, the concentric sleeve has selectively adjustable positions selected via the knob, movement of the sleeve between positions altering the direction of the air either towards or away from the mouthpiece of the valve.

6. A regulator according to claim 1 wherein said two baffles on said elongate member of the poppet are spaced apart and disposed approximately midway between the ends of the poppet.

7. A regulator according to claim 1 comprising:

means for creating a balance between the biasing force and the inlet to the housing by air continuously impinging on the second baffle immediately prior to exiting the flow path, when the poppet moves and fully opens the flow path, said balance creating means comprising at least one second air baffle being located proximate the flow path to the outlet.

8. A regulator according to claim 1 wherein air impinges predominately on a surface of the at least one second air baffle.

9. A regulator according to claim 1 wherein the means for providing a bias on the poppet is created by a helical spring.

10. A regulator according to claim 9 wherein the helical spring is concentric with a portion of the poppet and engages a surface on the at least one second air baffle.

11. A regulator according to claim 10 wherein the spring engages the second end of the poppet.

12. A regulator according to claim 1 wherein the means for providing a bias on the poppet is created by a helical spring;

the helical spring is concentric with a portion of the poppet and engages a surface on the at least one second air baffle; and, the first end of the poppet optionally comprises a baffle having an area less than a first cross sectional area of the flow path in the valve but greater in area than a second cross sectional area of the air supply to the flow path, said first end of the poppet acts as a closure for the housing inlet when the poppet is in the closed position and as an air baffle when the poppet is in the open position.

13. A regulator according to claim 1 wherein the concentric sleeve is made from a plastics material.

14. A regulator according to claim 1 wherein:

the concentric sleeve is made from a plastics material;

the knob has associated therewith gradations indicating the selectively adjustable positions for the concentric sleeve.

15. A regulator according to claim 1 wherein the first end has sealing means for sealing the inlet responsive to the poppet being in the closed position.

16. A breathing regulator for use in underwater breathing comprising:

a housing having a breathing chamber and an outlet, a valve means for enabling travel of air upon demand by a user, the valve means having a body, an inlet, and an outlet, wherein the air travels upon demand by the user through the inlet and outlet of the valve means, and then through the outlet of the housing;

a movable diaphragm means in the housing responsive a user's demand for air;

a venturi assisted air directing means for selectively determining a distance the air travels in the housing from the valve means outlet to the housing outlet, the venturi assisted air directing means comprising:

an opening in the valve means, and a rotatable concentric sleeve about the valve means body also having an opening therein, the concentric sleeve having adjustable placement between a first and a second selectable position, the position of the sleeve opening relative to the valve means body opening determining the air travel distance;

the first position of the sleeve opening aligning with the opening in the valve means body and resulting in a shortest travel distance between the valve means body outlet and the housing outlet;

movement of the sleeve opening towards the second position of the sleeve opening taking the sleeve opening out of alignment with the valve means body opening and thereby increasing the air travel distance by inhibiting the free flow of air through the openings.

17. A regulator according to claim 16 wherein the regulator further comprises a rotatable knob located on an exterior of the housing, the concentric sleeve being rotated responsive to rotation of the knob.

18. A regulator according to claim 17 wherein adjustment of the mechanical sleeve via the knob alters the direction of the air either towards or away from the mouthpiece of the valve.

19. A regulator according to claim 18 wherein the concentric sleeve is made from a plastics material.

20. A regulator according to claim 19 wherein the knob has associated therewith gradations indicating the available settings for the concentric sleeve.

* * * * *